United States Patent [19]

Walsh

[11] Patent Number: 4,892,662
[45] Date of Patent: Jan. 9, 1990

[54] MEMBRANE PROCESSING METHOD

[76] Inventor: James W. Walsh, 3832 Beech Ave., Baltimore, Md. 21211

[21] Appl. No.: 266,831

[22] Filed: Nov. 3, 1988

Related U.S. Application Data

[60] Division of Ser. No. 942,054, Dec. 15, 1986, which is a continuation-in-part of Ser. No. 694,773, Jan. 25, 1985, abandoned.

[51] Int. Cl.$^4$ .............................................. B01D 13/00
[52] U.S. Cl. ..................... 210/649; 210/232; 210/321.84
[58] Field of Search ............... 210/232, 649, 321.84; 204/403; 435/6, 172.3

[56] References Cited

U.S. PATENT DOCUMENTS

| | | | |
|---|---|---|---|
| 3,332,216 | 7/1967 | Stern | 55/158 |
| 3,488,690 | 1/1970 | Ross et al. | 210/321 |
| 3,490,523 | 1/1970 | Esmond | 165/166 |
| 3,660,280 | 5/1972 | Rogers | 210/22 |
| 3,757,947 | 9/1973 | Wakefield et al. | 210/240 X |
| 3,823,827 | 7/1974 | Radford | 210/238 |
| 4,401,566 | 8/1983 | Igari et al. | 210/351 |
| 4,455,370 | 6/1984 | Bartelsman et al. | 204/403 X |

OTHER PUBLICATIONS

"Detection of Specific Sequences Among DNA Fragments Separated by Gel Electrophoresis," by E. M. Southern in J. Mol. Biol. (1975), vol. 98, pp. 503-17.

Primary Examiner—Frank Spear
Attorney, Agent, or Firm—Cushman, Darby & Cushman

[57] ABSTRACT

A membrane processing method for subjecting solid support membranes used in the analysis and investigation of membrane bound specimens, such as molecules and molecule fragments of DNA and RNA, includes a flexible wall jacket, a membrane support for supporting the membrane within the jacket, and a frame upon which the jacket is mounted for processing. The jacket includes an open end through which the membrane support is inserted and fluid ports for introducing and removing fluid from the interior of the jacket. The membrane support is defined by sheets of open weave fabric that support the membrane to define a multitude of fluid pathways across the opposite surfaces of the membrane and also define lateral distribution channels on opposite edges of the membrane support. The frame includes attachment points for attachment to the jacket and a resilient clamp allows convenient sealing of the open end of the jacket prior to the introduction and removal of treatment fluids. The treatment fluids may be introduced into the jacket by connecting one fluid port to a vacuum source to create a below ambient pressure in the jacket and by introducing a treatment fluid through the other port. The fluid flows through the numerous fluid pathways on the opposite surfaces of the membrane to effect time and cost efficient treatment of the membrane.

11 Claims, 5 Drawing Sheets

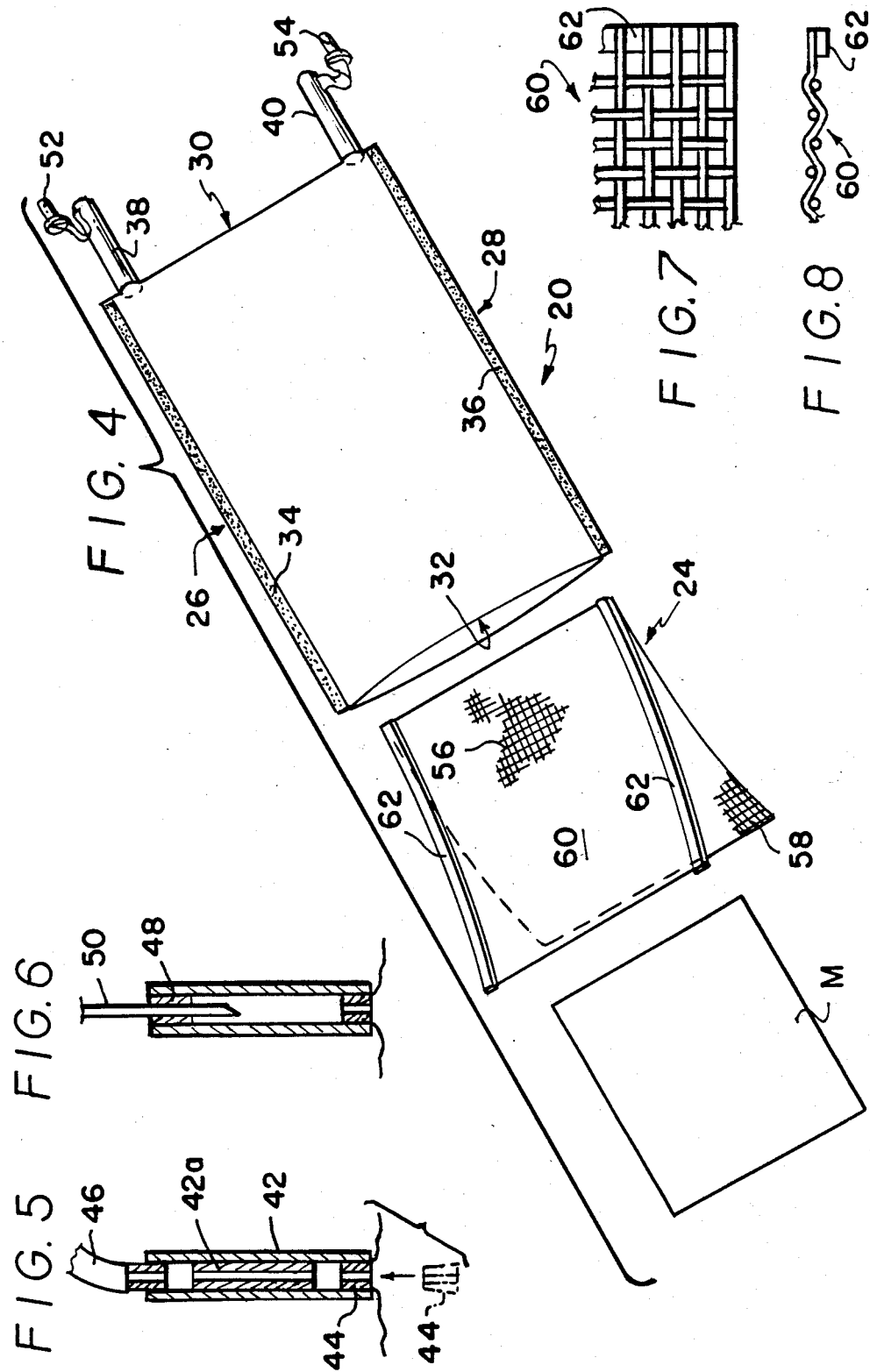

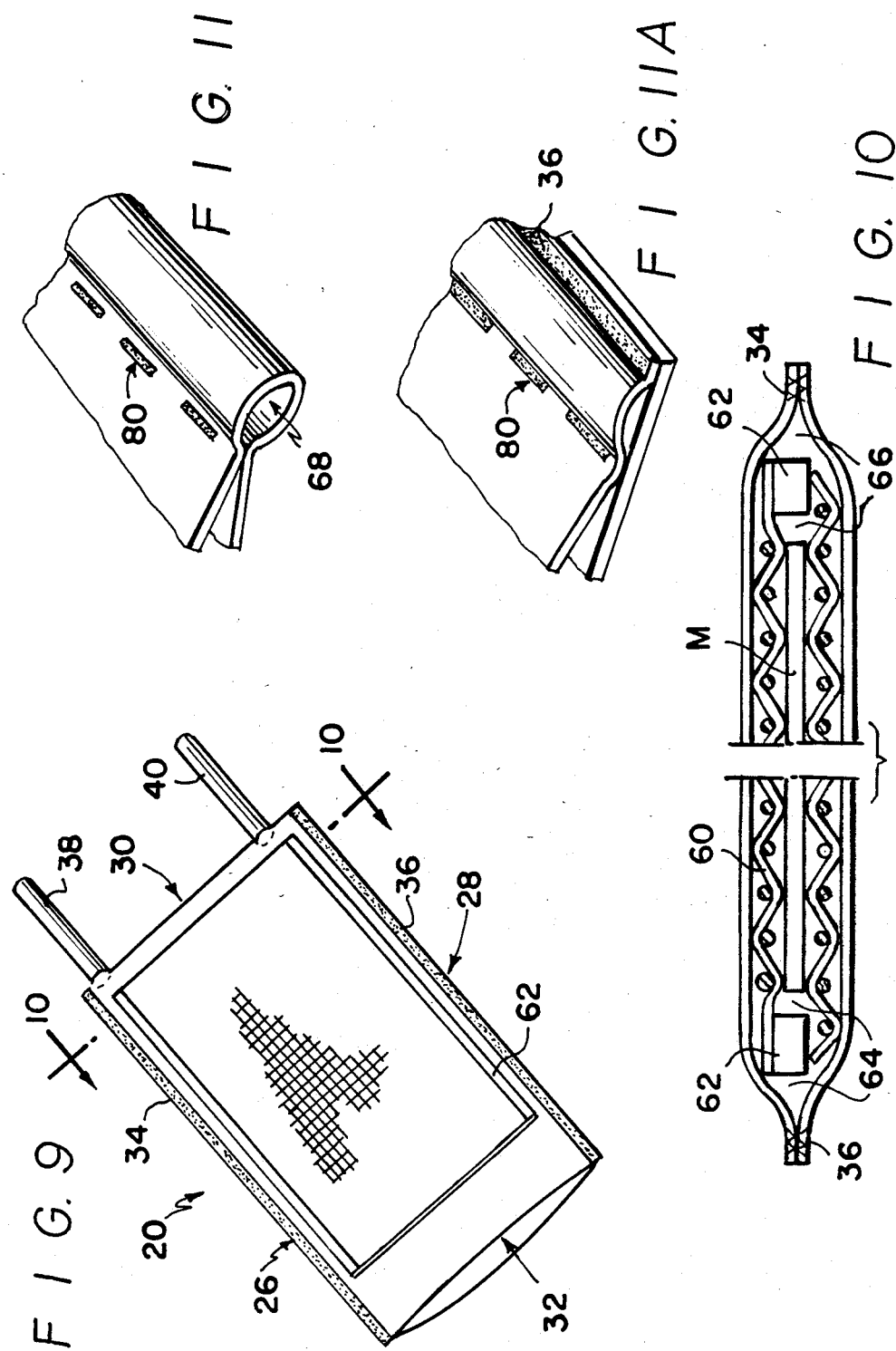

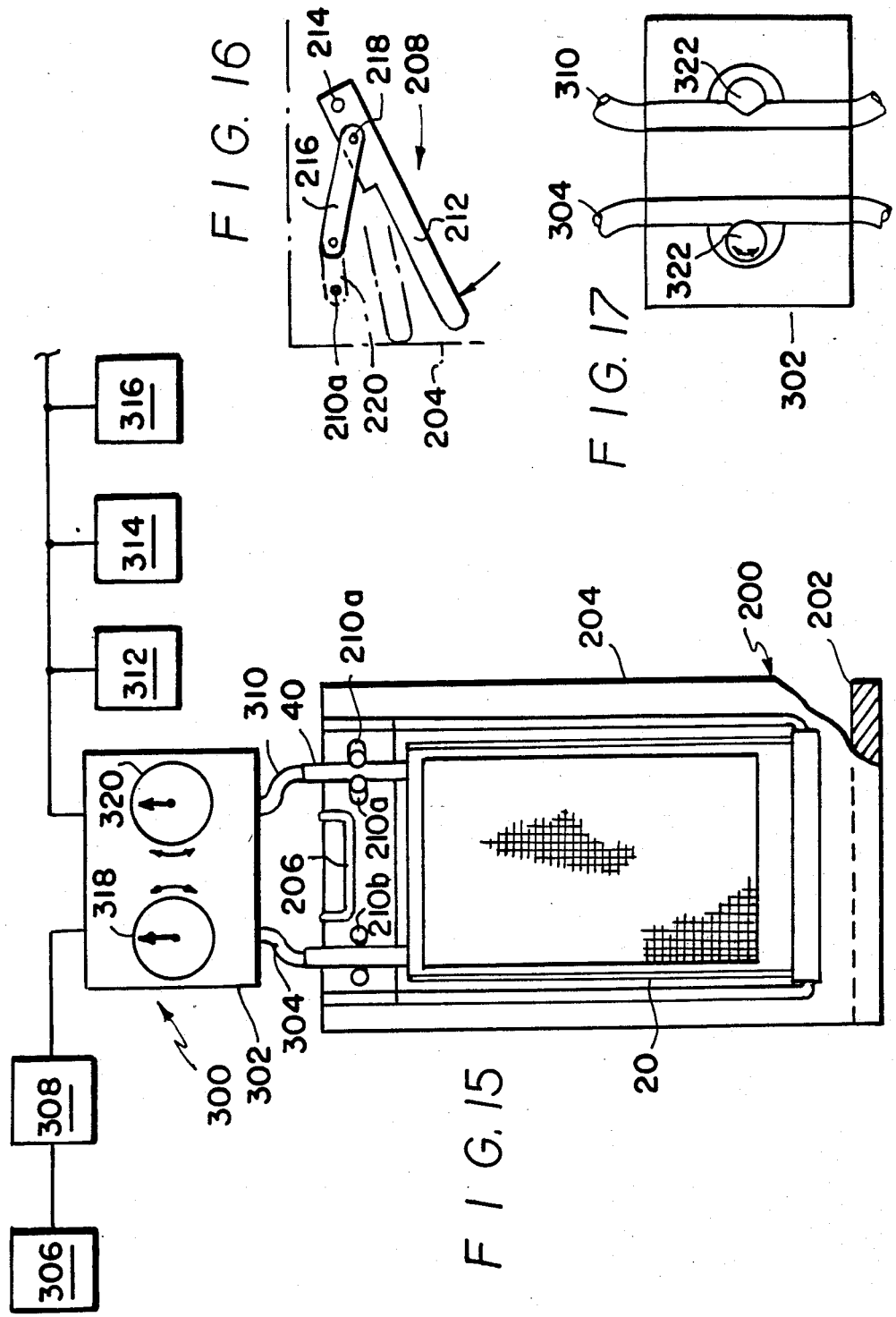

MEMBRANE PROCESSING METHOD

REFERENCE TO RELATED APPLICATIONS

This application is a divisional of commonly owned and copendng U.S. patent application Ser. No. 942,054 filed by applicant on Dec. 15, 1986 and entitled "Flexible Jacket Membrane Processing Apparatus," which application is a continuation of U.S. patent application Ser. No. 694,773 filed by applicant on Jan. 25, 1985 and entitled "Membrane Processing System and Method," now abandoned. The subject matter of the present application is related to that disclosed in co-pending U.S. patent application Ser. No. 776,050, filed by applicant on Sept. 13, 1985 and entitled "Membrane Batch-Processing System and Method."

BACKGROUND OF THE INVENTION

The present invention relates generally to methods of analysis and investigation which utilize a solid support in the form of membranes or similar media upon which selected specimens are transferred to or otherwise placed for analysis and evaluation. More particularly, the present invention relates to and is suited for use in those areas of biotechnology and molecular biology that utilize membranes upon which selected specimens are deposited for analysis, investigation, hybridization, and the like, such specimens including molecules and molecule fragments of DNA, RNA, and proteins.

Many laboratory and analytical procedures involve the use of a sheet-like membrane, such as nitrocellulose, treated nitrocellulose, and similar materials, upon which one or more specimens are deposited with the membrane then subjected to further processing steps to analyze, identify, or isolate selected of the specimens. For example, in the investigation of nucleic acids, the study of the structure and characteristics of DNA and RNA, and the function of selected enzymes in dividing DNA and RNA molecules into fragments of varying size, the use of sheet-like membranes, particularly those of nitrocellulose, are central to isolating selected fragments having certain characteristics. Various membrane-utilizing processes have been developed for the investigation of nucleic acids; these processes have in common the step of transferring or otherwise depositing DNA or RNA specimens onto a membrane. The membrane is then subjected to subsequent processing in accordance with the particular methodology of the process. For example, in one process, termed the "Southern" blot procedure, fragments of DNA molecules of unlike size are electrophoretically separated into groupings of similar size. The fragments are then transferred to a nitrocellulose membrane for subsequent processing to produce a visible indication, for example, by autoradiograph, of the position on the membrane of the target fragments. In another process, termed the "dot" blot procedure, fragments of DNA molecules of unlike size are separated, for example, by ultra-centrifuging or column chromatography, into separate samples of like size. The separate samples are then deposited onto a nitrocellulose membrane with each sample occupying a dot-like area on the membrane. The membrane is then subjected to additional processing steps to again yield an autoradiograph which indicates the position of the target fragments on the membrane.

The present invention can be best understood in the context of the Southern blot procedure, selected steps of which are illustrated in FIGS. 1, 2, and 3. In the Southern blot procedure, as well as the other membrane utilizing procedures, source DNA molecules are cleaved into fragments of differing length by restriction enzymes that recognize selected sites on the DNA molecule and cleave the molecule at those recognition sites into molecule fragments of varying lengths. As part of the analytical process, the molecular fragments are separated as a function of their length. In the Southern blot procedure, the molecular fragments are electrophoretically separated. As schematically illustrated in FIG. 1, an agarose or polyacrylamide gel slab G is prepared with electrodes, schematically illustrated at E1 and E2, aligned along opposite edges of the slab. The source mixture of molecule fragments is deposited on the slab G and the electrodes are connected to a suitable source of electrical energy to apply a directed electric field across the gel slab between the two electrodes. Since the molecule fragments have a net charge, they will migrate through and across the slab G toward the oppositely charged electrode with the speed of transportation being a function, in part, of the molecular weight of the fragment. In time, molecules of similar size will be grouped with one another in spaced apart, band-like groupings with the largest fragments grouped relatively close to the initial position and the smallest fragments grouped furthest from the initial position to thus effectively separate the molecules as a function of size.

After the molecule fragments have been electrophoretically separated as a function of fragment size, the fragments are transferred from the gel to a membrane M having an affinity for the particular molecule fragments. Where DNA fragments have been separated in the gel slab G, a sheet-like membrane M of nitrocellulose is laid upon one surface of the gel. Where other molecules, such as RNA are separated, another membrane having an affinity to RNA, such as diazobenzyloxymethyl cellulose (DBM) paper or aminophenylthioether (APT) paper activated to the diazo-form (DPT), may be used.

Once the membrane M has been applied to the gel slab G, the molecules in the gel matrix can be transferred to the membrane M by the Southern transfer method by establishing a capillary transfer through the gel and the contiguous membrane M. The gel slab G and the membrane M are placed upon the upper surface of an absorbent material S, which may take the form of a stack of blotting papers, saturated with a blotting buffer solution. A dry absorbent material D, which may also take the form of a stack of absorbent blotting sheets, is placed on the upper side of the membrane M so that a capillary transfer is established from the saturated material S through the gel slab G and the membrane M to the dry or unsaturated absorbent material. As the blottng buffer passes from the saturated to the unsaturated materials, the electrophoretically separated DNA molecules are eluted from the gel matrix and transferred to the membrane M with the molecular fragments binding to the membrane. This transfer process can be assisted electrophoretically by establishing an electric field across the absorber stack to assist in moving the molecules from the gel matrix to the membrane M. Regardless of the particular gel-to-membrane transfer mechanism employed, the resulting membrane M will have groupings of DNA molecule fragments bound thereto.

The membrane M is then subjected to a number of fluid treatment steps to identify a particular grouping of target DNA fragments on the membrane. Typically, the transferred DNA fragments are thermally "fixed" to the membrane M by heating at a selected temperature for a period of time sufficient to effect fixing. In order to locate a group of particular target fragments bound to the membrane M, a solution of DNA or RNA "probe" fragments complementary to the target fragments is prepared with the probe fragments coupled to a radioactive tracer material. The membrane M is then washed in the probe solution, for example, by immersion in a capped bottle or heat-sealed plastic bag containing the probe solution, for an incubation period sufficient to allow the radio-tagged probe fragments to hybridized with their complementary target fragments on the membrane. Once sufficient time for annealing has lapsed, the membrane M is then washed and treated in a series of buffer solutions, such as ribonuclease, at differing temperatures and concentrations designed to remove the excess unhybridized probe solution. The resulting membrane M is dried and retains only the original DNA fragments and the hybridized probe and target radio-tagged fragments. Thereafter, the membrane M is processed to yield a visible indication of the location of the annealed target/probe molecules. Typically, the visible indication is obtained by laying the membrane against one side of a radiation sensitive film so that the film is exposed by beta particle radiation from the radioactive tag. The location of the hybridized probe/target molecule fragments on the membrane M is revealed by the developed film.

Throughout the above described processing steps, the typically thin (e.g. 0.001 inch) and structurally weak membrane is subject to many manual handling steps over a relatively long period of time. Even where higher strength membranes are available, conventional membrane-dependent procedures require a rather high level of skill to insure valid and reproducible results and to minimize physical damage to or contamination of the membrane. Also, the use of membranes is not conducive to time and cost efficiencies that would allow transfer of the membrane-based methodologies to clinical, industrial, and agricultural applications, or other applications where cost and time effectiveness is imperative.

SUMMARY OF THE INVENTION

In view of the above, it is an object of the present invention, among others, to provide a method for improving generally the processing of solid support membranes and support media used in the analysis and investigation of membrane-supported specimens.

It is also an object of the present invention to improve methodologies for processing membranes used in molecular biology by decreasing time and costs associated with such processes.

It is another object of the present invention to provide improved methodology for processing membranes used in molecular biology to reduce the opportunity for mishandling and contamination.

It is a further object of the present invention to provide improved methodology for processing membranes and similar materials used in molecular biology so as to provide a convenient method for the fluid processing of the membrane.

It is still a further object of the present invention to provide improved methodology for the processing of membranes which are better suited for clinical, industrial, and agricultural applications and machine-automated processing compared to prior methodology.

In accordance with these objects and others, the present invention provides methodology for improved procedures involving the use and treatment of solid support membranes having molecular specimens thereon. A membrane processing container is defined by a flexible wall jacket having a sealable open end and fluid ports in communication with the interior of the jacket and through which various fluids can be introduced into and removed from the container. A sample membrane is supported on at least one side by a membrane support having surface characteristics that define a multitude of fluid pathways across the surface of the membrane. The supported membrane is placed in the flexible wall jacket which is then sealed so that the membrane can be exposed to various fluids introduced into and removed from the jacket through the fluid ports. In accordance with one feature of the present invention, the pressure in the flexible wall jacket is reduced to a pressure below local ambient so that the flexible walls collapse against the supported membrane with the membrane support cooperating with the flexible walls of the jacket to define fluid distribution channels along at least two edges of the supported membrane. Treatment fluids are introduced into one of the fluid ports and flow into one of the fluid channels defined along an edge of the supported membrane and flow across the surface of the membrane via the multiple pathways to the other fluid channel defined along the other edge of the membrane to the outlet port.

In the preferred form, the membrane treatment container is defined by a flexible plastic jacket that is closed at one end and open at the other. The membrane support is defined by a sheet of finely woven or perforated flexible plastic that overlays the opposite surfaces of the membrane with the interstices of the woven material defining multiple fluid pathways across the opposite surfaces of the membrane. The edges of the woven support are each provided with an edge spacer that cooperates with the flexible walls to create a fluid channel along opposite edges of the supported membrane with each channel communicating with respective fluid entry and removal ports for introducing or removing fluid from the container. The container and the membrane are mounted on a wire frame that includes an elongated clamp for sealing the open end of the container. Treatment solutions, including probe, buffer, and wash solutions, can then be introduced into one of the fluid ports to be distributed in the connected fluid channel along one edge of the supported membrane with the fluid then flowing through the multiple pathways across the opposite surfaces of the membrane to the other fluid channel on the opposite edge of the membrane for removal though the other fluid port.

It is contemplated that the best mode of the present invention is in analytical procedures involving the identification of selected molecules bound to a membrane, especially DNA and RNA molecules and molecule fragments, and proteins. For example, a nitrocellulose membrane is sandwiched between the open-weave sheets of the membrane support and utilized in the Southern blot procedure whereby DNA molecules are eluted by capillary action from a gel and transferred through the open-weave material of the membrane support to the membrane. The mesh supported membrane is then inserted into the open-ended flexible plastic jacket. The plastic jacket is mounted in the wire frame which includes a clamp for sealing the open end of the jacket and support points for attachment to the fluid ports. Fluid communication is achieved with the interior of the jacket, e.g., by attaching one of the ports to a fluid supply and the other of the ports to a vacuum source using flexible tubing or, where desired, using a hypodermic needle penetrating a septum provided in one or both of the fluid ports. The container and frame are then mounted on a stand and the flexible walls of the container are collapsed onto the mesh-supported membrane by creating a below ambient pressure differential through one of the ports. The strips provided on the opposite edges of the support mesh cooperate with the collapsed flexible walls of the container to define fluid channls on the opposite lateral edges of the support mesh with each channel in fluid communication with respective ports and with each other via the multitude of fluid pathways extending across the opposite surfaces of the membrane.

Various solutions, including radio-tagged or color-yielding probe solutions, buffer solutions, and wash solutions can be introduced into one of the ports to flow along the fluid channel defined on one edge of the mesh-supported membrane and then across both surfaces of the membrane via the multiple fluid pathways created by the surface characteristics of the mesh to the fluid channel on the opposite lateral edge and then to the outlet port.

The present invention thus provides methodology for generally improving procedures involving the handling and treatment of membrane-bound specimens, particularly procedures involving the analysis of membrane-bound DNA, RNA, and proteins, in such a way that the procedures are more time, material, and cost efficient to provide improved procedures better suited for clinical, industrial, and agricultural applications and eventual automation. The improved procedures consequent to the present invention provide greater immunity to mishandling and damage of the specimen-bound membrane as well as reduced vulnerability to contamination.

Other objects and further scope of applicability of the present invention will become apparent from the detailed description to follow, taken in conjunction with the accompanying drawings, in which like parts are designated by like reference characters.

BRIEF DESCRIPTION OF THE DRAWING

FIG. 4 is an exploded view of a membrane processing container in accordance with the present invention;

FIG. 5 is an enlarged detail view, in cross section, of a first embodiment of a fluid port;

FIG. 6 is an enlarged detail view, similar to that of FIG. 5, of a second embodiment of a fluid port;

FIG. 7 is an enlarged detail view of a portion of a membrane support element illustrated in FIG. 4;

FIG. 8 is an enlarged end view of a portion of the membrane support element illustrated in FIG. 7;

FIG. 9 is an isometric view of the elements of FIG. 4 in their assembled relationship;

FIG. 10 is an enlarged end view, in cross section, taken along line 10—10 of FIG. 9, of the assembled membrane processing container in which selected cross sections have been enlarged out of proportion for reasons of illustration;

FIG. 11 is a partial isometric view of an alternate construction for a portion of the membrane processing container;

FIG. 11a is a partial isometric view of another alternate construction for a portion of the membrane processing container;

FIG. 15 is an isometric view of a test stand upon which the assembled membrane processing container and mounting frame are mounted for processing;

FIG. 16 is a front partial view of the test stand of FIG. 15 with the front panel shown in dotted line illustration to reveal a pinch mechanism; and FIG. 17 is a rear view of a controllable valving block illustrated in FIG. 15.

DESCRIPTION OF THE PREFERRED EMBODIMENT

Figure 2:
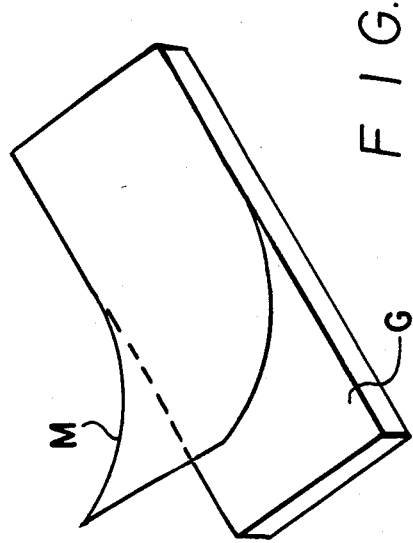
FIG. 2 is an isometric view of the gel slab of FIG. 1 with a membrane being laid upon one surface of the gel slab.
Figure 3:
FIG. 3 is a side elevation view of the gel and membrane of FIG. 2 in a capillary transfer arrangement to effect capillary elution of DNA fragments from the gel and transfer to the membrane.
Figure 1:
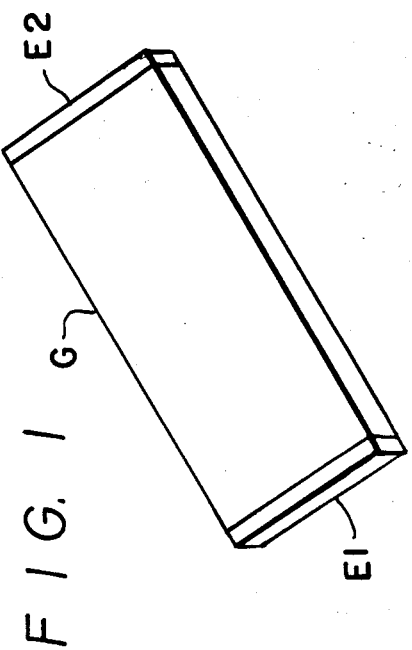
FIG. 1 is an isometric view, in schematic form, of a gel slab useful for the electrophoretic separation of DNA molecule fragments.

The method of the present invention is useful for the processing and treatment of solid support membranes as used in various laboratory and analytical procedures, particularly as used in molecular biology where molecules of selected materials, such as DNA, RNA, and proteins, are bound to or otherwise supported upon a membrane and subjected to various processing steps. The present invention will be disclosed herein in the context of those procedures involving nucleotides, such as procedures used to identify molecules and molecule fragments of DNA and RNA.

As shown in FIG. 4, a membrane processing container in accordance with the present invention is designated generally by the reference character 20 and includes a bag- or sac-like jacket 22 and a membrane support 24 for supporting the membrane M as described below.

The jacket 22 has opposite lateral sides 26 and 28, an upper closed end 30, and a normally open lower end 32. The jacket 22 is formed from a flexible, fluid-impervious material such as a polyethylene film having a film thickness less than 20 mils, with a three to five mil thickness preferred, that is inert to the processing fluids or a functionally equivalent material. The jacket has length and width dimensions sufficient to accept the membrane support 24; a length of seven or so inches and a width of five or so inches being preferred. The jacket 22 may be formed form a rectangular sheet of polyethylene film that is folded along a mid-line to define the closed upper end 30 and sealed on its opposite lateral sides 26 and 28 by thermal, ultrasonic, adhesive, or similar bonding techniques, as indicated by the stippled seams 34 and 36, to form the jacket. In the alternative, the jacket 22 may be formed as a sleeve from a length of seamless plastic tubing that is sealed at one end to form the closed upper end 30. It is not necessary that the entire jacket 22 be formed from a flexible material. For example, the jacket 22 can be formed from a rigid or semi-rigid sheet upon which another, flexible sheet is joined on three sides to yield an open-ended container having a flexible wall.

Fluid ports 38 and 40 are provided in the jacket 22 to introduce, remove, and assist in distributing fluids along the opposite lateral edges of the jacket 22 as described more fully below. In the preferred embodiment, the fluid ports 38 and 40 are mounted at the closed end 30 of the jacket 22 although the ports can be mounted at other positions consistent with the fluid introducing, removing, and distribution functions.

As shown in FIGS. 5 and 6, each port 38 and 40 can be formed from a hollow polyethylene or similar plastic tube 42 and a hollow frusto-conical insert 44. The lower end of each tube 42 is positioned on the exterior side of the closed end 30 of the jacket 22 while the respective insert 44 is positioned in the interior of the jacket. The insert 44 is then forced into the lower end of the tube 42 with the plastic film being stretched over the surface of the insert 44 to conform to the frusto-conical interface between the insert and its mating tube. In practice, the frusto-conical insert 44 expands the lower end of the tube 42 to create an interference fit that captures the film between the two components with the film also rupturing at the narrow end of the insert 44 to provide an economical yet reliable leak-proof fluid connection to the interior of the jacket 22. The ports 38 and 40 may be connected to other apparatus, described more fully below, by flexible tubing terminated by a "Luer" slip fitting 46, as illustrated in FIG. 5. As described below, the fluid flow through the ports is interrupted by pinching the tube 42 that defines each port. In accordance with one feature of the present invention, a hollow valving insert 42a is contained within the bore of the tube 42 that defines the ports. The valving insert 42a is fabricated from a lower density material that is more readily deformable than the material from which the tube 42 is fabricated. In the preferred embodiment, the tube 42 is formed from a yieldable polyethylene while the valving insert is formed from a lower densty and more readily deformable PVC. Where desired, a septum 48, as shown in FIG. 6, may be provided in the bore of the tubular ports 38 and 40 with fluid communication established through a hypodermic needle 50 that penetrates the septum 48 in the usual manner. Removeable caps 52 and 54 (FIG. 4) connected by suitable tethers (unnumbered) to the respective ports 38 and 40 can be provided to close the ports as desired.

The membrane support 24, as shown in FIG. 4, is defined by top and bottom sheets 56 and 58 of a porous material. In the preferred form, the membrane support 24 is defined by a rectangular sheet of an open weave polyethylene fabric 60 that is folded or creased along a mid-line to define the top and bottom sheets 56 and 58. The membrane support 24 is dimensioned with a width somewhat narrower and a length somewhat shorter than that of the jacket 22 to allow convenient insertion and removal through the open lower end 32 of the jacket. As shown in FIGS. 7 and 8, the open-weave fabric 60 has orthogonal weft and woof threads that create numerous interstitial spaces on the upper and lower faces of each sheet 56 and 58. In the preferred embodiment, a fabric thickness of five to ten mils woven from a 75 to 95 micron fiber with a thread count of between 90 and 120 per inch for the weft and woof threads has been found satisfactory. While an open-weave polyethylene fabric 60 is preferred for the top and bottom sheets 56 and 58, other materials that perform in a functionally equivalent manner are suitable. Other suitable materials include perforated sheets or webs having textured, undulating, or corrugated surface characteristics that cooperate with the membrane M to form multiple fluid pathways across the surface of the membrane.

As shown in FIGS. 4, 7, and 8, at least one strip-like edge spacer 62 is provided on each lateral edge of the membrane support 24. The edge spacers 62, in their preferred form, are defined by a narrow strip of polyethylene or similar plastic that is thermally, ultrasonically, or adhesively bonded to the edge or margin of the fabric 60. The spacers 62, as shown in FIG. 10, have a thickness dimension sufficient to prevent the flexible walls of the jacket 22 from contacting one another along the lateral edges of the membrane support 24 to thus create lateral flow channels 64 and 66 within the jacket 22 on opposite lateral sides of the membrane support 24. The lateral flow channels 64 and 66 are in fluid communication with the fluid ports 38 and 40, as explained below. In the preferred embodiment, a single spacer strip 62 on each lateral edge of one of the support sheets 56 or 58 has been found satisfactory for creating the lateral flow channels 64 and 66. While spacers 62 are preferred for forming the lateral flow channels 64 and 66, the channels may also be established by placing an elongated distribution tube (not shown) on each side of the membrane support 24, or, as shown in FIG. 11, by forming a periodically interrupted linear seal generally parallel to and adjacent each lateral edge of the jacket 22 and in such a manner to form a self-sustaining fluid distribution manifold 68. Where one wall of the jacket is formed from a rigid or semi-rigid sheet, as illustrated in FIG. 11a, the flexible sheet may be also attached using a periodically interrupted liner seal 80' that is spaced from the edge seam 36.

The membrane processing container 20 is assembled by first placing a membrane M between the top and bottom sheets 56 and 58 of the membrane support 24. The membrane M may be one onto which specimen molecules have been eluted from a gel matrix in accordance with the above-described Southern transfer procedure. In the alternative and in accordance with one feature of the present invention, the membrane M may be one without specimens and onto which specimens are transferred while the membrane M is contained in the membrane support 24. In this latter case, the membrane support 24 and its membrane M are laid upon one side of a gel matrix containing electrophoretically separated DNA molecules. The Southern transfer procedure is then used to elute the DNA molecules from the gel through the interstices of the membrane support 24 to the membrane M. The use of the membrane support 24 as part of the Southern blot procedure protects the membrane M from damage with only a minimal reduction in transfer efficiency or resolution of the resulting autoradiograph.

After the specimen has been transferred to the membrane M, the membrane support 24 and the supported membrane are inserted, as shown in FIG. 9, through the open end 32 of the jacket 22. As shown in FIG. 10, the membrane M is confined between and structurally supported by the top and bottom sheets 56 and 58 of the membrane support 24 which, in turn, are confined between the flexible walls of the jacket 22. The undulations of the woven top and bottom sheets 56 and 58 on the opposite sides of the membrane M create a multitude of fluid flow pathways across the opposite surfaces of the membrane M and the porosity of the membrane M permits fluid flow through the membrane from one side to the other. The spacers 62 prevent the opposed walls of the jacket 22 from contacting one another along the lateral edges of the membrane support 24 to create and maintain the fluid flow channels 64 and 66 along the lateral edges of the membrane support 24.

Figure 12:
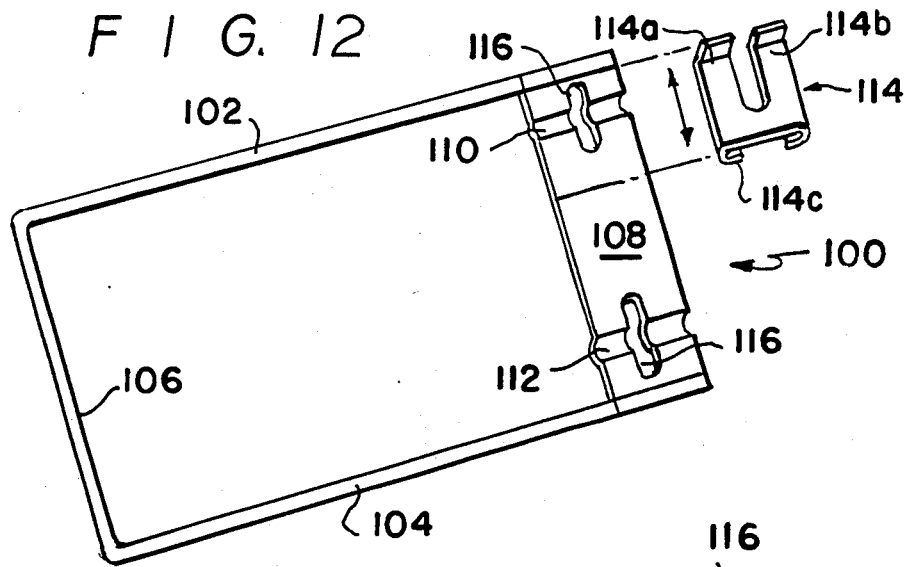
FIG. 12 is an isometric view of a mounting frame for supporting the assembled test container of FIG. 9.
Figure 13:
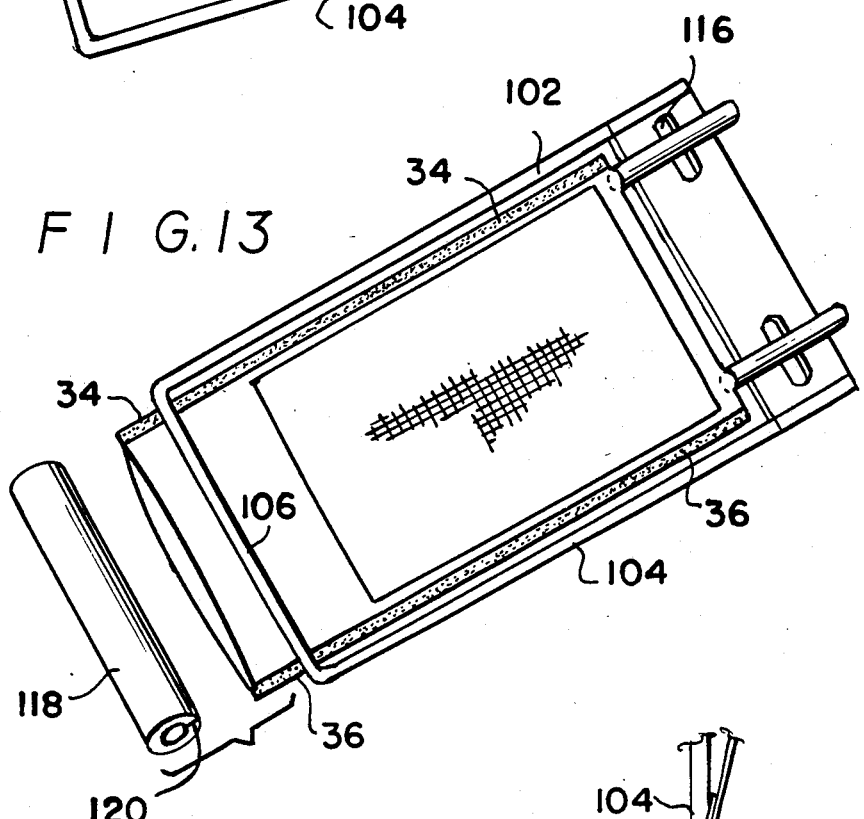
FIG. 13 is an isometric view of the mounting frame of FIG. 12 and the test container of FIG. 9 in their assembled state.
Figure 14:
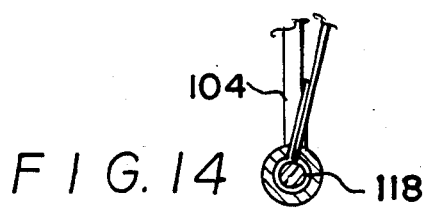
FIG. 14 is an enlarged detail view, in cross section, illustrating the manner by which the membrane processing container is sealed.

The assembled membrane processing container 20, including the membrane M, the membrane support 24, and the jacket 22, are mounted upon a support frame shown in FIGS. 12, 13, and 14 and designated generally therein by the reference character 100. The support frame 100 is designed to both seal the lower end 32 of the jacket 22 in a fluid-tight manner and provide a mounting that can be conveniently handled. The support frame 100 is formed with spaced, generally parallel side legs 102 and 104 joined at their lower ends by a connecting leg 106 and at their upper ends by a bridge 108. The side and connecting legs 102, 104, and 106 are preferably formed from a rigid metal wire while the bridge 108 is formed from a sheet metal stamping that is mechanically joined to the wire side legs 102 and 104 by any suitable means.

The bridge 108 is formed with two spaced apart semi-cylindrical channels 110 and 112 that are dimensioned to receive the tubular fluid ports 38 and 40, respectively. The bridge 108 is provided with elongated slots 116 that extend orthogonally across each channel 110 and 112. Retaining clamps 114, one of which is shown in FIG. 12, are used to hold each fluid port in its respective receiving channel. The retaining clamps 114 are bifurcated to define port-retaining tabs 114a and 114b separated by a U-shaped slot 116' that is registerable with the respective slot 116 formed in the bridge 108. The retaining clamps 114 are mounted on the bridge 108 prior to its being secured to the legs 102 and 104 and include turned edges 114c that maintain the clamps 114 on the bridge 108 in a slidable manner. The channels 110 and 112 may also be dimensioned to receive their respective tubular ports 38 and 40 in a resilient interference fit that allows each fluid port to be "snapped" in and out of its receiving channel. As explained below, portions of a flow pinch-off mechanism extend through each slot 116 on opposite sides of the fluid ports 38 and 40 to allow the fluid flow in each port to be interrupted or resumed.

As shown in FIGS. 13 and 14, when the fluid ports 38 and 40 are in position in their respective channels 110 and 112, the lower open end 32 of the jacket 22 initially lies across the connecting leg 106. In order to seal the jacket 22, the lower end of the jacket is wrapped around the connecting leg 106 and held in place by a length of resilient tubing 118 formed from a plastic, rubber, or similar elastomeric material. The tubing 118 includes a longitudinal slit 120 and can be separated or splayed apart along its slit 120 and pushed upon the wrapped connecting leg 106, as shown in FIG. 14, to capture and seal the lower end 32 of the jacket 22 to the connecting leg 106.

The frame 100 and the mounted membrane processing container 20 can be mounted on a support stand of the type shown in FIG. 15 and designated generally by the reference character 200. The support stand 200 includes a base 202 and an upright panel 204. The membrane processing container 20 is placed against the upright panel 204 and a formed wire spring, bail or clamp 206 is placed over the two to resiliently secure the bridge 108 to the upper end of the panel 204. The panel 204 includes pinch clamps 208 (FIG. 16) that have cylindrical posts 210a and 210b that extend through the elongated slots 116 formed in the bridge 108 with the posts 210a and 210b positioned on opposite sides of each tubular fluid port. As shown on the left side of FIG. 15, the posts 210a and 210b can be positioned in a spaced apart relationship to allow unrestricted fluid flow through the port 38 or, as shown on the right side of FIG. 15, the post 210b can be moved toward the stationary post 210a to pinch-off and interrupt any fluid flow in the port 40. The pinch clamps 208 are mounted on the back side of upright panel 204 and, as shown in FIG. 16, the pinch clamps include a lever 212 pivoted at one end by a pin 214 and a connecting link 216 pivotally connected to the lever 212 by a pin 218. The opposite end of the connecting link 216 carries the pin 210b for guided movement in a slot 220 (broken line illustration) formed in the panel 204. The pin 210a is stationary and cooperates with the moveable pin 210b to pinch off the tubular port when the lever 212 is manually moved from the solid line to the broken line positions of FIG. 16. The geometry of the lever 212 and the connecting link 216 can be configured so that the clamp 208 operates as a momentary action clamp or configured so that the clamp operates as an over-center toggle ON/OFF clamp.

In order to process the membrane M using the apparatus described above and in accordance with the method of the present invention, the membrane M upon which the specimen is deposited must first be thermally fixed by baking at a temperature high enough to effect fixing. The fixing is preferably accomplished while the membrane M is mounted in the membrane support 24. Thereafter, the membrane M, the membrane support 24 and the jacket 22 are assembled to the frame 100 as described above and the frame is mounted to the test stand 200. The membrane M is then subjected to a number of fluid treatment steps, described below, to produce a visible indication of the location of desired target fragments on the membrane M.

As shown in FIG. 15, the ports 38 and 40 of the membrane processing container 20 are connected to a fluid processing system 300 that is shown in generalized schematic form. The system 300 includes a valve unit 302 having a fluid line 304 connected from the port 38 through the valve unit 302 to a vacuum source 306 and a fluid receiving trap 308 and another fluid line 310 connected from the port 40 through the valve unit 302 to individually valved sources of fluid 312, 314, 316, etc. which may contain probe, wash, buffer or other fluids related to the particular process or process steps.

As shown in FIG. 15, the valve unit 302 includes manually operable knobs 318 and 320 by which the flow through the fluid lines 304 and 310 can be controlled. As shown in FIG. 17, the rear of the valve unit 302 includes two spaced parallel slots (unnumbered) which receive the fluid lines 304 and 310. The knobs 318 and 320 are each secured to rotatably mounted shafts (not shown) with an eccentrically mounted valving cam 322 secured to the opposite ends of the shafts. Rotation of the knobs 318 and 320 causes the connected valving cam 322 to press against the typically resilient fluid lines to control flow through the lines.

In order to process the membrane M, a probe solution containing radio-tagged DNA or RNA molecules complementary to the target molecules is introduced through the port 40 into the container 20 with any trapped air aspirated from the container by the vacuum source 306. The introduction of the probe solution and the aspiration of the trapped air may also be effected by hypodermic syringe. The pinch mechanisms 208 are then operated to cause the posts 210a and 210b to pinch off both fluid ports 38 and 40 and the caps 52 and 54 used to close the respective port. The sealed membrane processing container 20 and frame 100 are placed in an oven or water bath for an incubation period sufficient to effect annealing of the probe and target fragments. Where incubation is effected in a water bath, the weight of the frame 100 prevents the sealed membrane container 20 from floating.

After annealing is completed, the membrane processing container 20 and the frame 100 are remounted on the support stand 200 and the bulk of the probe solution is removed by aspiration from the membrane processing container 20.

The membrane M is then washed by applying a vacuum to the port 38 from the vacuum source 306 while allowing a wash solution to be introduced into the port 40 from one or more of the fluid sources 312, 314, or 316. The application of the vacuum causes the flexible walls of the jacket 22 to be pressed against the membrane support 24, as shown in FIG. 10, with the spacer strips 62 maintaining the lateral channels 64 and 66. If desired, a properly dimensioned resilient elastomeric pad (not shown) can also be used to press the flexible wall of the jacket against the membrane support 24. The wash solution is transported through the fluid port 40 into and along the lateral flow channel 66. The wash solution then flows through the multiple fluid pathways created by the interstices of the membrane support 24 across the opposite surfaces of the membrane M to the other lateral flow channel 64 where the wash solution passes through the other fluid port 38. While the pressure differential existing between the fluid ports 40 and 38 motives the flow of the wash solution, it is also believed that the multiple fluid pathways assist by functioning as capillaries. Additional washing may be provided using wash solutions of differing concentrations. The washings result in the removal of the unhybridized probe solution leaving the membrane M with its original fragments and the annealed radio-tagged probe and target fragments. The multiple fluid pathways defined across the surfaces of the membrane are believed to expose all portions of the membrane to the fluid flow in such a way that the fluid treatment is efficiently accomplished in a time and fluid efficient manner without exposing the membrane to any potentially damaging fluid flow conditions.

The various fluid treatment steps can be conducted in a serial manner or with one or more intermediate "air" washings. In the latter case, air is allowed to enter the inlet port to cause the liquid from the prior fluid treatment to be entirely discharged from the jacket 22 prior to the introduction of the next fluid in the treatment sequence. The air washing aids in the removal of any residual liquids by entraining droplets in the air flow and transporting the droplets to the exit port.

After the washing sequence is completed, the fluid port 40 may be closed, for example, by the pinch mechanism 208 or by the operation of the knob 320, and the membrane M dried in situ as a result of the applied vacuum. After drying, the entire fluid processing container 20 can be placed against one side of a radiation sensitive film to effect exposure with the developed film revealing the location on the membrane M of the target fragments. In practice, the presence of the membrane support 24 and the flexible wall of the jacket 22 between the membrane M and the film does not materially affect the resolution of the resulting autoradiograph.

In the preferred embodiment described above, the membrane support has been descibed as a separate component that cooperates functionally with the flexible wall jacket to define the multiple flow channels across the surface of the membrane. As can be appreciated, the membrane support can be secured in the jacket or formed integrally with the jacket. For example, the membrane support can be installed within the jacket and permanently held in place by mechanically connecting the fabric of the membrane support with the flexible wall of the jacket, for example, by thermal, ultrasonic, adhesive, or similar techniques. In addition to bonding or otherwise securing the membrane support to the interior of the jacket, the membrane support and the flexible walls of the jacket can be functionally integrated in a single flexible wall material by forming the jacket from a material having surface characteristics, such as undulations, channels, corrugations, or the functional equivalent, that define the multiple fluid pathways.

As can be appreciated from the above, the present invention provides improved methodology for those procedures which utilize a membrane-bound specimen in such a way that the procedures are more time, material, and cost efficient to provide procedures better suited for clinical, industrial, and agricultural applications and eventual automation.

Thus it will be appreciated from the above that as a result of the present invention, a highly effective membrane processing system and method is provided by which the principal objective, among others, is completely fulfilled. It will be equally apparent and is contemplated that modification and/or changes may be made in the illustrated embodiment without departure from the invention. Accordingly, it is expressly intended that the foregoing description and accompanying drawings are illustrative of preferred embodiments only, not limiting, and that the true spirit and scope of the present invention will be determined by reference to the appended claims.

What is claimed is:

1. A method for treating a membrane, comprising the steps of:
    engaging a membrane to be treated on at least one surface thereof with a membrane support that defines a plurality of pathways across the engaged surface of the membrane;
    containing the membrane and the membrane support within a flexible walled container having fluid distribution channels on at least two edges of the membrane and a fluid port in communication with each of the fluid distribution channels;
    introducing a fluid into one of the fluid ports for distribution into the associated fluid distribution channel; and
    establishing a pressure differential between the interior and the exterior of the container to cause the flexible walls of the container to press against the membrane support to maintain engagement of the membrane support with the membrane thereby allowing the introduced fluid to flow across the surface of the membrane through the plurality of pathways to the other port.

2. The method of claim 1, further comprising the step: removing the introduced fluid through the other port.

3. The method of claim 1, further comprising the step of:
applying a resilient pressure pad against the flexible wall of said container to press the membrane support against the membrane.

4. The method of claim 1, further comprising the step of:
introducing a second fluid into the one fluid port subsequent to the introduction of the first fluid.

5. The method of claim 4, further comprising the step of:
introducing air into the one fluid port between the introduction of the first and second fluids.

6. An improved method of eluting molecules and molecule fragments in a gel matrix onto a membrane and treating the membrane with a fluid, comprising the steps of:
engaging a membrane onto which molecules or molecule fragments are to be eluted on at least one side with a porous membrane support material that defines a plurality of pathways across the engaged surface of the membrane;
applying the membrane and membrane support to a gel matrix from which molecules and molecule fragments are to be eluted, the membrane support positioned intermediate the gel matrix and the membrane;
establishing a capillary transfer through the gel matrix, the membrane support, and the membrane to elute molecules and molecule fragments from the gel matrix, through the membrane support to the membrane; and
containing the membrane and the membrane support within a flexible walled container having fluid distribution channels on at least two edges of the membrane and a fluid port in communication with each of the fluid distribution channels;
introducing a fluid into one of the fluid ports for distribution into the associated fluid distribution channel; and
establishing a pressure differential between the interior and the exterior of the container to cause the flexible walls of the container to press against the membrane support to maintain engagement of the membrane support with the membrane thereby allowing the introduced fluid to flow across the surface of the membrane through the plurality of pathways to the other port.

7. The method of claim 6, further comprising the step of:
removing the introduced fluid through the other port.

8. The method of claim 6, further comprising the step of:
applying a resilient pressure pad against the flexible wall of said container to press the membrane support against the membrane.

9. The method of claim 6, further comprising the step of:
introducing a second fluid into the one fluid port subsequent to the introduction of the first fluid.

10. The method of claim 9, further comprising the step of:
introducing air into the one fluid port between the introduction of the first and second fluids.

11. An improved method of eluting molecules and molecule fragments in a gel matrix onto a membrane comprising the steps of:
engaging a membrane onto which molecules or molecule fragments are to be eluted on at least one side with a porous membrane support material;
applying the membrane and membrane support to a gel matrix from which molecules and molecule fragments are to be eluted, the membrane support positioned intermediate the gel matrix and the membrane; and
establishing a capillary transfer through the gel matrix, the membrane support, and the membrane to elute molecules and molecule fragments from the gel matrix, through the membrane support to the membrane.

* * * * *